(12) United States Patent
Nakanishi et al.

(10) Patent No.: US 7,557,241 B2
(45) Date of Patent: Jul. 7, 2009

(54) METHOD FOR PRODUCING α,β-UNSATURATED CARBOXYLIC ACID ESTER, α,β-UNSATURATED CARBOXYLIC ACID ESTER, AND LUBRICATING OIL ADDITIVE

(75) Inventors: Hideo Nakanishi, Kyoto (JP); Satoshi Utsui, Kyoto (JP); Tsuyoshi Yuki, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 0 days.

(21) Appl. No.: 11/709,482

(22) Filed: Feb. 22, 2007

(65) Prior Publication Data

US 2007/0173421 A1    Jul. 26, 2007

Related U.S. Application Data

(63) Continuation of application No. PCT/JP2005/014325, filed on Aug. 4, 2005.

(30) Foreign Application Priority Data

| Aug. 30, 2004 | (JP) | ............................. 2004-249407 |
| Mar. 6, 2006 | (JP) | ............................. 2006-059280 |

(51) Int. Cl.
   *C07C 69/52* (2006.01)
(52) U.S. Cl. ..................................................... 560/205
(58) Field of Classification Search ........................ None
   See application file for complete search history.

(56) References Cited

U.S. PATENT DOCUMENTS

| 2,798,850 | A | * | 7/1957 | Voigtman et al. ......... 210/502.1 |
| 2,936,284 | A | * | 5/1960 | Hakala et al. ............... 508/409 |
| 3,177,226 | A | * | 4/1965 | Horst et al. .................. 549/447 |
| 3,965,046 | A | * | 6/1976 | Deffeyes .................... 502/337 |
| 4,330,434 | A | * | 5/1982 | Hughes ...................... 502/168 |
| 5,233,119 | A | * | 8/1993 | Kallenbach et al. .......... 585/721 |
| 5,360,926 | A | | 11/1994 | Kouno et al. |
| 5,523,414 | A | * | 6/1996 | Kume et al. ................. 548/548 |
| 5,536,586 | A | * | 7/1996 | Tsushio et al. .............. 428/649 |
| 5,827,939 | A | | 10/1998 | Paumard |
| 5,912,385 | A | | 6/1999 | Kushibe et al. |
| 6,087,527 | A | * | 7/2000 | Niwa et al. .................. 560/190 |
| 6,624,124 | B2 | * | 9/2003 | Garmier ....................... 508/491 |
| 2003/0036488 | A1 | * | 2/2003 | Yuki et al. ................... 508/469 |
| 2003/0104955 | A1 | * | 6/2003 | Yuki et al. ................... 508/469 |
| 2004/0077509 | A1 | * | 4/2004 | Yuki et al. ................... 508/469 |

FOREIGN PATENT DOCUMENTS

| EP | 0 552 541 | | 7/1993 |
| IT | EP 570070 A 1 | * | 11/1993 |
| JP | 67006324 B | * | 7/1964 |
| JP | 54081212 | * | 6/1979 |
| JP | 54081212 A | * | 6/1979 |
| JP | 57175145 A | * | 10/1982 |
| JP | 06234701 A | * | 8/1994 |
| JP | 11-80082 | | 3/1999 |
| JP | 11-152248 | | 6/1999 |
| JP | 11-319574 | | 11/1999 |
| WO | 90/08127 | | 7/1990 |

OTHER PUBLICATIONS

Alvaro, et al., "Single-step preparation and catalytic activity of mesoporous MCM-41 and SBA-15 silicas functionalized with perfluoroalkylsulfonic acid groups analogous to Nafion®", Communications, Apr. 21, 2004, No. 8, p. 956-957.

Bossaert, et al., "Mesoporous Sulfonic Acids as Selective Heterogeneous Catalysts for the Synthesis of Monoglycerides", Journal of Catalysis, 1999, vol. 182, No. 1, p. 156-164.

Okita, et al.,"Preparation of Strong Acid-functionalized Mesoporous Silica and its Catalysis", Proceedings of the 84th Spring Meeting of the Chemical Society of Japan, Mar. 11, 2004, p. 453 with its partial translation.

Xingdong, et al.,"Preparation and Catalytic Activity of SBA-15 Mesoporous Silica Functionalized with Sulfonic Acid Groups", Chinese Journal of Catalysis, Sep. 2002, vol. 23, No. 5, p. 435-438.

* cited by examiner

*Primary Examiner*—Paul A Zucker
(74) *Attorney, Agent, or Firm*—Hamre, Schumann, Mueller & Larson, P.C.

(57) ABSTRACT

A method for producing an α,β-unsaturated carboxylic acid ester is provided in which an alcohol (A) is caused to react with an α,β-unsaturated carboxylic acid or a lower alkyl ester (B) of the α,β-unsaturated carboxylic acid in the presence of a sulfonic acid group-carrying inorganic porous material (α), and an α,β-unsaturated carboxylic acid ester obtained by the above-described method is provided that contains not more than 50 ppm of sulfur atoms based on a weight of the α,β-unsaturated carboxylic acid ester, not more than 2 mol % of by-product etherification products and not more than 1 mol % of by-product addition products based on the mole number of the α,β-unsaturated carboxylic acid ester. Such methods are a method for producing an α,β-unsaturated carboxylic acid ester that does not involve generation of a large amount of waste products and a method for producing a high-purity α,β-unsaturated carboxylic acid ester that causes only a smaller amount of by-products to be generated, and a high-purity α,β-unsaturated carboxylic acid ester is provided that contains only a smaller amount of catalyst residues and exhibits less metal corrosion behavior.

10 Claims, No Drawings

METHOD FOR PRODUCING α,β-UNSATURATED CARBOXYLIC ACID ESTER, α,β-UNSATURATED CARBOXYLIC ACID ESTER, AND LUBRICATING OIL ADDITIVE

TECHNICAL FIELD

The present invention relates to a method for producing an α,β-unsaturated carboxylic acid ester, and also to the α,β-unsaturated carboxylic acid ester. More specifically, the present invention relates to a method for producing an α,β-unsaturated carboxylic acid ester in which a solid acid is used as a catalyst, the α,β-unsaturated carboxylic acid ester obtained by the foregoing method, and a lubricating oil additive containing a polymer formed with the α,β-unsaturated carboxylic acid ester as an indispensable constituent monomer.

BACKGROUND ART

Conventionally, mineral acids (sulfuric acid, phosphoric acid, etc.) and sulfonic acids (p-toluene sulfonic acid, methane sulfonic acid, trifluoromethane sulfonic acid, etc.) usually are used as acid catalysts used in the reaction between alcohol and α,β-unsaturated carboxylic acids or lower esters thereof for production of α,β-unsaturated carboxylic acid esters.

However, in the case where such a Brønsted acid is used as a catalyst, complicated steps for removing a catalyst, for example, neutralization, washing with water, or adsorption, are needed after the reaction, and waste products are generated in a large amount. Besides, catalyst residues remain in the obtained carboxylic acid ester, and sometimes cause a problem of corrosion of a metal that the catalyst residues are in contact with, depending on the manner in which the ester obtained is used.

As a solution for such a problem, a method for producing an α,β-unsaturated carboxylic acid ester has been proposed in which one of various "solid acid" catalysts is used. The use of the "solid acid" as a heterogeneous catalyst facilitates the separation of the catalyst from a reaction product, thereby reducing waste products generated by neutralization, washing with water, etc.

As such a solid acid catalyst, the following have been proposed: ion exchange resins (sulfonated product of styrene-divinylbenzene copolymer, etc.) (see Patent Documents 1 and 2 shown below); solid super strong acids such as phosphotungstic acid (see Patent Document 3 shown below); and fluororesins containing sulfonic acid ("Nafion" produced by Du-Pont, etc.).

However, none of these solid acid catalysts exhibits satisfactory catalytic activity as a catalyst for α,β-unsaturated carboxylic acid esters, and tend to cause generation of by-products. Examples of the by-product include elimination reaction products (olefins generated when water is eliminated from monomolecular alcohols), etherified products (ethers generated by dehydrocondensation of bimolecular alcohols), and addition products (adducts generated by addition of alcohols to α,β-unsaturated groups). Therefore, these solid acid catalysts have a problem that the obtained α,β-unsaturated carboxylic acid esters have low purity.

Besides, there also is a problem that acidic components such as sulfur oxides that have eluted upon decomposition of a catalyst tend to remain, even though the amount is smaller than that in the case of a Brønsted acid.

Patent Document 1: U.S. Pat. No. 6,087,527
Patent Document 2: WO 90/08127
Patent Document 3: U.S. Pat. No. 5,827,939

DISCLOSURE OF THE INVENTION

Problem to be Solved by the Invention

It is an object of the present invention to provide a method for producing an α,β-unsaturated carboxylic acid ester that does not involve generation of a large amount of waste products.

It is another object of the present invention to provide a method for producing a high-purity α,β-unsaturated carboxylic acid ester that causes only a smaller amount of by-products to be generated.

It is still another object of the present invention to provide a method for producing an α,β-unsaturated carboxylic acid ester that contains only a smaller amount of catalyst residues and exhibits less metal corrosion behavior.

It is still another object of the present invention to provide a high-purity α,β-unsaturated carboxylic acid ester obtained by the above-described producing methods.

It is still another object of the present invention to provide a lubricating oil additive that is composed of a polymer formed with the above-described high-purity α,β-unsaturated carboxylic acid ester as an indispensable constituent monomer, and that has excellent demulsibility.

SUMMARY OF THE INVENTION

A method of the present invention for producing an α,β-unsaturated carboxylic acid ester comprises causing an alcohol (A) to react with an α,β-unsaturated carboxylic acid or a lower alkyl ester (B) of the α,β-unsaturated carboxylic acid in the presence of a sulfonic acid group-carrying inorganic porous material (α).

An α,β-unsaturated carboxylic acid ester of the present invention is obtained by causing an alcohol (A) to react with an α,β-unsaturated carboxylic acid or a lower alkyl ester (B) of the α,β-unsaturated carboxylic acid in the presence of a sulfonic acid group-carrying inorganic porous material (α), and the α,β-unsaturated carboxylic acid ester contains not more than 50 ppm of sulfur atoms based on a weight of the α,β-unsaturated carboxylic acid ester, not more than 2 mol % of by-product etherification products and not more than 1 mol % of by-product addition products based on a mole number of the α,β-unsaturated carboxylic acid ester.

DETAILED DESCRIPTION OF THE INVENTION

In the present invention, examples of the alcohol (A) (hereinafter "alcohol (A)" sometimes simply is referred to as "(A)") include monohydric alcohols (A1) and polyhydric alcohols (A2) having a valence of two or more.

Examples of the (A1) include the following:

(A11) saturated aliphatic monohydric alcohols [straight-chain or branched-chain alcohol having 1 to 36 carbon atoms such as methyl alcohol, ethyl alcohol, n-propyl alcohol, isopropyl alcohol, butyl alcohol, 2-ethylhexyl alcohol, octyl alcohol, nonyl alcohol, decyl alcohol, undecyl alcohol, dodecyl alcohol, tridecyl alcohol, tetradecyl alcohol, hexadecyl alcohol, octadecyl alcohol, nonadecyl alcohol, 2-decyl tetradecyl alcohol, 2-tetradecyl octadecyl alcohol, etc.];

(A12) unsaturated aliphatic monohydric alcohols [straight-chain or branched-chain alcohol having 2 to 36 carbon atoms such as vinyl alcohol, (meth)allyl alcohol, octenyl alcohol, decenyl alcohol, dodecenyl alcohol, tridecenyl alcohol, pentadecenyl alcohol, oleyl alcohol, gadoleyl alcohol, linoleyl alcohol, etc.];

(A13) alicyclic monohydric alcohols [alcohol having an alicyclic group and having 6 to 36 carbon atoms in total such as ethyl cyclohexyl alcohol, propyl cyclohexyl alcohol, octyl cyclohexyl alcohol, nonyl cyclohexyl alcohol, adamantyl alcohol, etc.];

(A14) monohydric phenols [phenols having a phenol ring and having 6 to 36 carbon atoms in total, such as phenol, cresol, t-butyl phenol, styrenated phenol, bromophenol, etc.]

(A15) monohydric alcohols having a nitrogen atom, a sulfur atom, and/or a halogen atom [above-described alcohols (A11) to (A14) a part of which is substituted with a group containing a nitrogen atom, a sulfur atom, and/or a halogen atom, for example, dimethyl aminoethanol, diethyl aminoethanol, morpholinoethanol, 2-chloroethanol, etc.]; and (A 16) alkylene oxide (hereinafter abbreviated as AO) adducts (the number of added moles: 1 to 50) of the above-described alcohols (A11) to (A15) [examples of AO include AO having 2 to 8 carbon atoms such as ethylene oxide (hereinafter abbreviated as EO), propylene oxide (hereinafter abbreviated as PO), 1,2- or 2,3-butylene oxide, tetrahydrofuran, and styrene oxide].

Examples of the (A2) include:

(A21) dihydric alcohols [alkylene glycols having 2 to 12 carbon atoms (ethylene glycol, 1,2-propylene glycol, 1,3-propylene glycol, 1,4-butylene glycol, 1,6-hexane diol, etc.); polyalkylene glycols having a polymerization degree of 2 to 1,000 (diethylene glycol, triethylene glycol, dipropylene glycol, polyethylene glycol, polypropylene glycol, polybutylene glycol, etc.); alicyclic diols (diols having a alicyclic group and having 6 to 36 carbon atoms in total, such as 1,4-cyclohexane dimethanol, hydrogenated bisphenol A, etc.), AO adducts (the number of added moles: 1 to 50) of the above-described dihydric alcohols, and AO adducts (the number of added moles: 2 to 30) of the above-described bisphenols (bisphenol A, bisphenol F, bisphenol S, etc.) (with the same AO as those described above being used)];

(A22) aliphatic polyhydric alcohols having a valence of three to eight or more [alkane polyols, intramolecular or intermolecular dehydration products (glycerol, trimethylol propane, pentaerythritol, sorbitol, sorbitan, polyglycerol, and dipentaerythritol), saccharides and derivatives thereof (sucrose and methyl glucocide), and AO adducts (the number of added moles: 1 to 50) of the above-described aliphatic polyhydric alcohols];

(A23) aromatic ring-containing polyhydric alcohols having a valence of three to eight or more [AO adducts (the number of added moles: 2 to 50) of trisphenols (trisphenol PA, etc.), AO adducts (the number of added moles: 2 to 50) of novolac resins (phenol novolac, cresol novolac, etc.)].

Among the examples of the (A), monohydric alcohols (A1), polyhydric alcohols having a valence of two to eight, and AO adducts of the same are preferred, among which the (A1) are more preferred. Among the examples of the (A1), the (A11), the (A12), the (A15), and AO adducts of the same are preferred, among which saturated aliphatic monohydric alcohols having 8 to 32 carbon atoms among the (A11) and AO (particularly EO) adducts of the same are more preferred since they allow for the production of high-purity products more easily.

Examples of a hydroxyl group contained in the (A) include primary hydroxyl groups and secondary hydroxyl group, among which primary hydroxyl groups are preferred.

Examples of α,β-unsaturated carboxylic acids (B1) in the α,β-unsaturated carboxylic acids and lower alkyl esters (B) (sometimes hereinafter simply referred to as "(B)") of the same in the present invention include aliphatic α,β-unsaturated monocarboxylic acids [(meth)acrylic acids, crotonic acid, etc.], and aliphatic α,β-unsaturated dicarboxylic acids (maleic acid, fumaric acid, itaconic acid, citraconic acid, etc.).

Further, examples of lower alkyl esters (B2) of α,β-unsaturated dicarboxylic acids include esters obtained from the (B1) and alcohols having an alkyl group having 1 to 4 carbon atoms (examples of such esters include methyl ester, ethyl ester, isopropyl ester, etc.).

Among the (B), the (B1) are preferred since high-purity esters are obtained. Among the (B1), aliphatic α,β-unsaturated monocarboxylic acids are more preferred since an amount of addition products among by-products is small. Among these acids, acrylic acids and methacrylic acids are particularly preferred since the polymerizability of α,β-unsaturated carboxylic acid ester to be obtained is enhanced.

The sulfonic acid group-carrying inorganic porous material (α) in the present invention (hereinafter sometimes simply referred to as "(α)") is an inorganic porous material on which a sulfonic acid group-containing compound is immobilized so as to be carried, and is used as a catalyst for the esterification reaction of the (A) and the (B).

A known inorganic porous material can be used as the inorganic porous material, and examples of the same include inorganic porous materials composed of one or more inorganic substances selected from the group consisting of silica, alumina, titania, magnesia, and zirconia.

Specifically, examples thereof include: silica gel as an inorganic porous material made of silica; alumina gel as an inorganic porous material made of alumina; zeolite as an inorganic porous material made of silica and alumina; and KYOWAAD (produced by Kyowa Chemical Industry Co., Ltd) that is a silica-alumina-based porous material as a commercially available absorbent, diatomaceous earth, etc. as other inorganic porous materials. Among these, silica, alumina, zeolite, and KYOWAAD are preferred from the viewpoint of catalytic activity, and silica gel and KYOWAAD are particularly preferred.

The inorganic porous material is usually a granular material, and examples of the shape thereof include an indefinite-shape particle form, a spherical particle form, and a pellet form.

Among these, the spherical particle form and the pellet form are preferred, and the spherical particle form is particularly preferred since pressure loss upon reaction by flow processing that will be described later is small.

The particle diameter of the inorganic porous material preferably is 1 to 8,000 μm, more preferably 10 to 6,000 μm, and particularly preferably 40 to 500 μm as a d50 (average particle diameter). In the case where the particle diameter is set to not less than 1 μm, the handling is facilitated. Besides, the range of not more than 8,000 μm is preferred from the viewpoint of catalytic activity. In the present invention, the d50 can be measured by the grain size distribution measurement method according to JIS K1150.

A specific surface area of the inorganic porous material determined by the Brunauer-Emmett-Teller (BET) equation (hereinafter referred to as BET specific surface area) preferably is not less than 30 $m^2/g$, more preferably 50 to 1,500 $m^2/g$, and particularly preferably 100 to 800 $m^2/g$. The reason why the specific surface area preferably is not less than 30 $m^2/g$ is that the catalytic activity increases while the side reaction decreases. In the present invention, the BET specific surface area can be measured by the specific surface area measurement method according to JIS K1150.

An aspect ratio of the inorganic porous material preferably is 1.0 to 1.25, more preferably 1.0 to 1.18, and particularly preferably 1.0 to 1.11. It should be noted that the aspect ratio is a ratio of the longest diameter of a particle with respect to the shortest diameter of the same, and a value closer to 1.0 indicates a higher sphericity. The aspect ratio in a range of 1.0 to 1.25 is preferred since the pressure loss upon reaction by flow processing that will be described later is small.

In the present invention, the aspect ratio can be measured by observing particles by a microscope, and measuring and averaging the shortest diameters and the longest diameters for 100 particles.

As a method for causing an inorganic porous material to carry a sulfonic acid group, the following method can be used: an inorganic porous material is caused to react with a sulfonic acid precursor group-containing compound (s) (hereinafter sometimes simply referred to as "(s)") that is transformable into a sulfonic acid group, and thereafter the sulfonic acid precursor group is transformed to a sulfonic acid group.

The (s) is a compound that has, in its molecule, a group that is reacted with a functional group on a surface of the inorganic porous material and a group that can be transformed to a sulfonic acid group.

Examples of the functional group on a surface of an inorganic porous material include a hydroxyl group, an amino group, and a carboxyl group. Among these, a hydroxyl group is preferred since the surface of an inorganic porous material can be modified easily.

On the other hand, examples of the group that is contained in the (s) and is reacted with a functional group on a surface of an inorganic porous group include a trialkoxy silyl group, a glycidyl group, and a carboxyl group in the case where the functional group on the surface is a hydroxyl group or an amino group, or alternatively, a trialkoxy silyl group, a glycidyl group, and an amino group in the case where the functional group on the surface is a carboxyl group.

Among these, a trialkoxy silyl group and a glycidyl group are preferred since such a group tends to accelerate the reaction with the functional group on a surface. Among these, a trialkoxy silyl group is particularly preferred.

Examples of a sulfonic acid precursor group that can be transformed to a sulfonic acid group contained in the (s) include a mercapto group (transformed by oxidation to a sulfonic acid group) and a phenyl group (transformed by sulfonation to a sulfophenyl group).

Examples of the (s) include a mercapto group-containing silane coupling agent (mercapto propyl trimethoxysilane, mercapto propyl triethoxysilane, etc.), a phenyl group-containing silane coupling agent (phenyl trimethoxysilane, phenyl triethoxysilane, diphenyl dimethoxysilane, etc.), and a phenyl group-containing glycidyl compound (phenyl glycidyl ether, nonyl phenyl glycidyl ether, etc.). Among these, a mercapto group-containing silane coupling agent is preferred.

The reaction between the silane coupling agent and the inorganic porous material can be carried out under various reaction conditions. For example, the reaction can be carried out as follows. A silane coupling agent of 30 to 60 percent by weight (wt %) based on the weight of an inorganic porous material is prepared, and heated and stirred in the presence of a solvent so that a trialkoxy silyl group in the silane coupling agent is caused to react with a functional group (e.g. a hydroxyl group) on the surface of the inorganic porous material. Then, an obtained product is purified, whereby a sulfonic acid group-carrying inorganic porous material ($\alpha$) is obtained.

As the solvent used in the reaction, an organic solvent (toluene, xylene, ethyl acetate, methyl ethyl ketone, acetone and/or lower alcohol having 1 to 4 carbon atoms, etc.) can be used, or alternatively, a mixture solvent containing water and such an organic solvent may be used.

Water preferably is used in a small amount, so that the activity of the hydroxyl group on the surface of the inorganic porous material and the silane coupling agent is accelerated. The ratio of water with respect to the silane coupling agent particularly preferably is not more than 3 times on a molar basis.

The amount to be used of the solvent based on the weight of the inorganic porous material normally is 80 to 300% (hereinafter "%" refers to "percent by weight" unless provided specifically), and preferably 100 to 250%.

The reaction temperature normally is 60 to 150° C., and the reaction may be performed while products derived from an alkoxy group generated (e.g. lower alcohols such as methanol, ethanol, etc.) are being removed.

After the reaction, a granular material is separated and collected by filtering or using a centrifugal separator or the like, and is washed with the above-described organic solvent several times so that non-reacted materials (non-reacted portions of the silane coupling agent, etc.) are removed. Then, the granular material obtained is dried under reduced pressure (normally at 100 to 120° C., at 10 to 20 mmHg, for 3 to 5 hours).

In order to transform a mercapto group to a sulfonic acid group after the reaction of a silane coupling agent containing the mercapto group, an oxidation reaction is carried out in the presence of a solvent. Examples of an oxidant used herein include various oxidants such as nitric acid, hydrogen peroxide, hypochlorites, potassium permanganate, chromic acid, and peroxides, among which hydrogen peroxide is preferred. As the foregoing solvent, normally acetone, lower alcohols having 1 to 4 carbon atoms, acetonitrile, pyridine, chloroform, and/or dichloromethane are used. The reaction temperature normally is 0 to 100° C. The oxidation reaction with use of hydrogen peroxide can be performed under the conditions described in U.S. Pat. No. 5,912,385.

In order to sulfonate a phenyl group after causing reaction of a silane coupling agent containing the phenyl group, various sulfonating methods are applicable. As a sulfonating agent, the following can be used, for example: concentrated sulfuric acid; fuming sulfuric acid; sulfur trioxide; chlorosulfuric acid; fluorosulfuric acid; or amidosulfonic acid. In such a case, the following can be used as a solvent: acetic acid; acetic anhydride; ethyl acetate; acetonitrile; dichloroethane; and/or carbon tetrachloride. The reaction temperature normally is −10 to 180° C.

Irrespective of which reaction is carried out, the oxidation reaction or the sulfonation reaction, the same operations as those described above (separation and collection, washing, and drying) are carried out as a purifying operation after the reaction, whereby a sulfonic acid group-carrying inorganic porous material ($\alpha$) can be obtained.

Among the methods for producing the ($\alpha$), the method in which a mercapto group-containing silane coupling agent is caused to react with an inorganic porous material and thereafter it is transformed to a sulfonic acid group is preferred.

The ($\alpha$) preferably has an acid value of 5 to 250 mgKOH/g, more preferably 10 to 150 mgKOH/g, and particularly preferably 15 to 100 mgKOH/g.

In the case where the acid value is not less than 5 mgKOH/g, catalytic activity is improved, thereby allowing the esterification reaction to be accelerated with use of a catalyst in a smaller amount. In the case where the acid value is not more than 250 mgKOH/g, a side reaction is reduced.

The acid value of the ($\alpha$) can be measured by soaking the ($\alpha$) in ion exchange water, adding sodium hydroxide in excess to the same and stirring the mixture, and subjecting the same to neutralization titration with a 0.1 N aqueous solution of hydrochloric acid.

The ($\alpha$) is substantially in the same shape as that of the inorganic porous material before carrying a sulfonic acid group, and preferable ranges of its d50, BET specific surface area, and aspect ratio also are identical to those of the inorganic porous material before carrying a sulfonic acid group.

The ($\alpha$) has a d50 preferably in a range of 1 to 8,000 µm, more preferably in a range of 10 to 6,000 µm, and particularly preferably 40 to 500 µm. In the case where the d50 is not less than 1 µm, the handling is facilitated, while the d50 of not more than 8,000 µm is preferable from the viewpoint of catalytic activity.

The ($\alpha$) preferably has a BET specific surface area of not less than 30 $m^2/g$, more preferably 50 to 1,500 $m^2/g$, and particularly preferably 100 to 800 $m^2/g$. The reason why the specific surface area preferably is not less than 30 $m^2/g$ is that the catalytic activity increases while the side reaction decreases.

The ($\alpha$) preferably is in a spherical particle form having an aspect ratio of 1.0 to 1.25, more preferably 1.0 to 1.18, and particularly preferably 1.0 to 1.11. The ($\alpha$) preferably is in a spherical particle form having an aspect ratio in a range of 1.0 to 1.25 since pressure loss upon reaction by flow processing that will be described later is small.

In the method for producing an unsaturated carboxylic acid ester according to the present invention, an equivalent ratio between the (A) and the (B) in the case where the (A) and the (B) are caused to react with each other is normally 1:3 to 3:1, preferably 1:2 to 2:1, more preferably 1:1.5 to 1.5:1, and particularly preferably 1:1.5 to 1:1.02.

From the viewpoint of improving the reaction rate, it is advantageous that either one of the (A) and the (B) that can be removed more easily is used in excess, and after the reaction is completed, the excess portion of either the (A) or the (B) is removed.

In the method for producing an unsaturated carboxylic acid ester according to the present invention, a polymerization inhibitor may be added for the purpose of preventing polymerization of unsaturated groups.

Examples of the polymerization inhibitor include phenol-type polymerization inhibitors (hydroquinone, hydroquinone monomethyl ether, catechol, cresol, di-t-butyl cresol, di-t-butyl phenol, tri-t-butyl phenol, etc.), and amine-type polymerization inhibitors (phenothiazine, diphenylamine, alkylated diphenylamine, etc.).

Among these, phenol-type polymerization inhibitors are preferred.

The amount to be added of the polymerization inhibitor based on the total weight of the (A) and the (B) normally is 0.001 to 2%, preferably 0.01 to 1%, more preferably 0.01 to 0.5%, and particularly preferably 0.01 to 0.2%.

The amount to be used of the ($\alpha$) based on the total weight of the (A) and the (B) normally is 0.1 to 70%, preferably 1 to 60%, more preferably 2 to 50%, and particularly preferably 3 to 40%.

The use of the ($\alpha$) of 0.1% or more is preferable since the esterification reaction is accelerated efficiently by doing so, and the use of the same of not more than 70% is preferable due to the economic advantages.

Further, the amount to be used of the ($\alpha$) is set so that a ratio of an equivalent of sulfonic acid groups in the ($\alpha$) with respect to an equivalent of the (A) used is preferably 0.005 to 0.3, and more preferably 0.01 to 0.2. The equivalent ratio preferably is not less than 0.005 since it is advantageous regarding the reaction velocity, while the equivalent ratio preferably is not more than 0.3 since in this case the side reaction is suppressed.

The esterification reaction can be performed by either of batch processing or flow processing.

In the case of batch processing, the ($\alpha$), the (A), and the (B), as well as a solvent as required, are put in a reaction vessel, heated and stirred, so that the reaction is allowed to advance while water or lower alcohol that is generated therein is being removed. After the reaction is completed, the reaction product is separated from the ($\alpha$) by decantation, filtering, centrifugation, etc. In the case where either the (A) or the (B) is used in excess, the excess portions are removed prior to or after the separation of the ($\alpha$), whereby the unsaturated carboxylic acid ester can be obtained.

The esterification reaction temperature normally is 60 to 180° C., preferably 80 to 160° C., and more preferably 100 to 140° C. The reaction temperature preferably is 60° C. or above from the viewpoint of the reaction velocity, and 180° C. or below in order to suppress a side reaction.

The reaction time normally is 10 minutes to 24 hours, preferably 30 minutes to 10 hours, and particularly preferably 1 to 5 hours.

As a solvent, the following can be used: hydrocarbon-type solvents (aromatic hydrocarbons such as toluene and xylene); ketone-type solvents (methyl ethyl ketone, methyl isobutyl ketone, etc.); and ether-type solvents (tetrahydrofuran, etc.). Among the reaction solvents, hydrocarbon-type solvents are preferred since water generated by the reaction can be separated and removed easily therefrom.

As a method for removing water or lower alcohol generated, the following are preferred: a method of distillation under a normal or reduced pressure; a method of separation or centrifugation; a method of bringing the same into contact with a dehydrator such as a molecular sieve, magnesium sulfate, etc.; and a method of membrane separation using a selective membrane such as a water separation membrane. In the case of the above-described batch processing, the method of distillation under a normal or reduced pressure is preferred.

In the case of flow processing, an esterification reaction can be caused by causing a mixture of the (A) and the (B) adjusted to a predetermined temperature to pass through a column filled with the ($\alpha$), a fixed bed, a fluidized bed, etc.

An unsaturated carboxylic acid ester also may be obtained by distilling a reaction mixture that has been passed through once. However, a producing method composed of the following two steps (1) and (2) is preferred since it increases the reaction rate: a step (1) of causing the (A) and the (B) to react with each other in the presence of the ($\alpha$); and a step (2) of removing water or lower alcohol generated by the reaction between the (A) and the (B) from a reaction mixture.

Particularly, by repeating the steps (1) and (2), the reaction rate can be increased further. The temperature of the mixture of the (A) and the (B) that is passed through in the step (1) normally is set to 60 to 180° C., preferably 80 to 160° C., and more preferably 100 to 140° C. The temperature preferably is 60° C. or above from the viewpoint of the reaction velocity, and 180° C. or below in order to suppress a side reaction.

The average passage time per one passage in the step (1) (average time of contact between the catalyst and the reaction liquid) normally is 0.1 to 60 minutes, preferably 0.2 to 10 minutes, and more preferably 0.5 to 5 minutes. As a method for removing water or lower alcohol in the step (2), the following method can be used: a method of distillation by a continuous evaporator; a method of distillation under a normal or reduced pressure by using a reaction vessel equipped with a condenser; or a method of dehydration by using a water separation membrane, by centrifugation, or by using a dehydrate. Among these, the continuous evaporator, a reaction vessel equipped with a condenser, or a combination of these preferably is used from the viewpoint of production efficiency.

The steps (1) and (2) normally are repeated 1 to 500 times, preferably 3 to 200 times, and more preferably 5 to 100 times.

In the producing method of the present invention, it is possible to dissolve oxygen in the reaction liquid for the purpose of inhibiting the polymerization of the (B) and the product obtained. As a supply source of oxygen, oxygen gas, air, or a mixture of air and nitrogen (hereinafter sometimes simply referred to as "mixture gas") can be used, and it is possible to dissolve oxygen in the reaction liquid by passing such a gas therethrough. For ensuring safety, air or a mixture gas is preferred, among which a mixture gas is particularly preferred.

A mixture volume ratio of air and nitrogen in a mixture gas normally is 1:9 to 9:1, preferably 1:9 to 5:5, and particularly preferably 2:8 to 4:6. An increase in the ratio of air is preferred for enhancing the effect of polymerization prohibition, whereas an increase in the ratio of nitrogen is preferred for decreasing discoloration of a product.

An amount of passage of air or a mixture gas per 1 kg of the sum of the (A) and the (B) preferably is 1 to 5,000 mL/min, more preferably 20 to 1,000 mL/min, particularly preferably 30 to 500 mL/min.

As a method for passing air or a mixture gas in the case of batch processing, a method of constantly passing the same from a bottom of a reaction vessel during esterification reaction can be used.

In the case of flow processing, the passage of the gas may be carried out during the step (1), during the step (2), or with respect to a reaction product in a pipe toward the step (1) or a pipe toward the step (2). Among these, the passage of the gas during the step (2) is particularly preferred from both of the viewpoints of the reaction velocity and the polymerization inhibition. In the step (2), it is preferable to pass air or a mixture gas constantly.

The purity of an unsaturated carboxylic acid ester obtained in the present invention normally is not less than 95%, and preferably not less than 98%.

Examples of impurities include non-reacted alcohols, elimination reaction products (olefins generated when water is eliminated from monomolecular alcohols, etc.), by-product etherification products (ethers generated from bimolecular alcohols by dehydrocondensation), by-product addition products (adducts generated by addition of alcohols to α,β-unsaturated groups, etc.), and sulfur atom-containing compounds (sulfur oxides eluted by decomposition of catalysts, etc.). It should be noted that a polymerization inhibitor is present, though it is not an impurity but an additive.

The content of a non-reacted alcohol based on the mole number of an α,β-unsaturated carboxylic acid ester normally is not more than 5 mol %, and preferably not more than 2 mol %.

The content of an elimination reaction product based on the mole number of an α,β-unsaturated carboxylic acid ester normally is not more than 2 mol %, and preferably not more than 0.1 mol % (the detection limit).

The content of a by-product etherification product based on the mole number of an α,β-unsaturated carboxylic acid ester preferably is not more than 2 mol % (more preferably not more than 1.5 mol %), and the content of a by-product addition product based on the mole number of an α,β-unsaturated carboxylic acid ester preferably is not more than 1 mol % (more preferably not more than 0.8 mol %).

Regarding a sulfur atom-containing compound, the content of sulfur atoms contained in the compound (hereinafter abbreviated as "S content") based on the weight of an α,β-unsaturated carboxylic acid ester normally is not more than 50 ppm, and preferably not more than 20 ppm (detection limit).

As the polymerization inhibitor, one or more types of polymerization inhibitors selected from the group consisting of the above-described phenol-type polymerization inhibitors and amine-type polymerization inhibitors can be used.

The content of a polymerization inhibitor based on the weight of an α,β-unsaturated carboxylic acid ester is 0.001 to 0.2%, and preferably 0.01 to 0.06%.

It should be noted that the contents of an α,β-unsaturated carboxylic acid ester, a non-reacted alcohol, an elimination reaction product, a by-product etherification product, and a by-product addition product can be quantified by measuring a $H^1$-NMR of a product and analyzing the same. The S content can be quantified by using an inductively coupled high-frequency plasma spectrometry device (hereinafter abbreviated as "IPC device") "ICPS-8000" (manufactured by Shimadzu Corporation).

Since the α,β-unsaturated carboxylic acid ester of the present invention has a high purity and has polymerizable unsaturated groups, it can be used suitably as a material monomer for various types of polymers.

Polymers obtained by using the α,β-unsaturated carboxylic acid ester of the present invention as one type of monomer can be used as various types of resins, resin modifiers, binders for use in pressure-sensitive adhesives, vehicles for use in paints, viscosity index improvers for use in lubricating oils, pour-point depressants for use in lubricating oils, and various types of additives.

In the case where a polymer obtained by using the α,β-unsaturated carboxylic acid ester of the present invention as one type of monomer is used as a lubricating oil additive, it is preferable that the α,β-unsaturated carboxylic acid ester is a (meth)acrylic acid alkyl ester (a) with an alkyl group having 10 to 36 carbon atoms, formed with an alcohol having 10 to 36 carbon atoms as the alcohol (A) and a (meth)acrylic acid or a lower alkyl ester of the same as the alcohol (B).

The lubricating oil additive of the present invention is a lubricating oil additive formed with a polymer (P) that is formed with the above-described (a) as an indispensable constituent monomer, in which the (a) is not less than 45 wt %, preferably not less than 50 wt % from the viewpoints of demulsibility and solubility in a base oil, and more preferably not less than 60 wt % among the entire constituent monomers forming the polymer (P).

In the (a), the content of sulfur atoms is not more than 50 ppm based on the weight of the (a), and the by-product etherification product and the by-product addition product are not more than 2 mol % and not more than 1 mol %, respectively, based on the mole number of the (a).

Particularly when the polymer (P) is prepared so that the content of sulfur atoms in the polymer (P) is not more than 50 ppm, preferably not more than 30 ppm, and more preferably not more than 20 ppm, a lubricating oil composition containing the (P) excels in not only the viscosity index improving ability, the low-temperature viscosity, the pour-point depressing ability, and the shearing stability, but also the demulsibility in particular. The demulsibility is an effect that a lubricating oil composition is resistant to emulsification even when a trace quantity of water is mixed in the lubricating oil composition, whereby the lubricity and the responsibility are prevented from being impaired.

Examples of the (a) include (meth)acrylic acid alkyl esters (a1) in which an alkyl group has 10 to 15 carbon atoms, and (meth)acrylic acid alkyl esters (a2) in which an alkyl group has 16 to 30 carbon atoms.

Examples of the (a1) include n-decyl (meth)acrylate, iso-decyl (meth)acrylate, n-undecyl (meth)acrylate, n-dodecyl (meth)acrylate, 2-methyl undecyl (meth)acrylate, n-tridecyl (meth)acrylate, n-tetradecyl (meth)acrylate, 2-methyl tridecyl (meth)acrylate, n-pentadecyl (meth)acrylate, 2-methyl tetradecyl (meth)acrylate, and (meth)acrylic acid ester of alcohol produced by oxosynthesis [e.g. products with trade names of "Dobanol 23" (produced by Mitsubishi Chemical Corporation), "NEODOL 23" (produced by Shell Chemical Co.), "TRIDECANOL" (produced by Kyowa Hakko Chemical Co., Ltd.), "OXOCOL 1213" (produced by Nissan Chemical Industries, Ltd.), "Dobanol 45" (produced by Mitsubishi Chemical Corporation), "NEODOL 45" (produced by Shell Chemical Co.), "OXOCOL1415" (produced by Nissan Chemical Industries, Ltd.)].

Among the examples of the (a1), (meth)acrylic acid alkyl esters having a straight-chain or branched-chain alkyl group having 12 to 15 carbon atoms, and mixtures of two or more of these are preferred.

Examples of the (a2) include n-hexadecyl (meth)acrylate, n-octadecyl (meth)acrylate, n-eicosyl (meth)acrylate, n-docosyl (meth)acrylate, 2-methylpentadecyl (meth)acrylate, 2-hexyldecyl (meth)acrylate, 2-methyl hexadecyl (meth)acrylate, 2-octyl decyl (meth)acrylate, 2-hexyl dodecyl (meth)acrylate, 2-methyl heptadecyl (meth)acrylate, 2-methyl octadecyl (meth)acrylate, 2-octyl dodecyl (meth)acrylate, and 2-decyl tetradecyl (meth)acrylate.

Among the examples of the (a2), (meth)acrylic acid alkyl esters having a straight-chain alkyl group having 16 to 18 carbon atoms, 2-decyl tetradecyl (meth)acrylate, and mixtures of two or more of these are preferred.

The lubricating oil additive of the present invention may be formed with a single polymer of the (a) described above alone, but it is preferable from the viewpoint of the viscosity index improving effect that the lubricating oil additive is composed of a copolymer obtained by copolymerizing the (a) with a monomer other than the (a).

Examples of the monomer other than the (a) include the following monomers (b) to (e):

(b) (Meth)acrylic Acid Alkyl Esters in which an Alkyl Group has 1 to 9 Carbon Atoms:

Examples of the (b) include:

(b1) (meth)acrylic acid alkyl esters in which an alkyl group has 1 to 4 carbon atoms such as methyl (meth)acrylate, ethyl (meth)acrylate, n-propyl (meth)acrylate, iso-propyl methacrylate, n-butyl (meth)acrylate, iso-butyl (meth)acrylate, and sec-butyl (meth)acrylate; and (b2) (meth)acrylic acid alkyl esters in which an alkyl group has 5 to 9 carbon atoms such as n-pentyl (meth)acrylate, iso-pentyl (meth)acrylate, sec-pentyl (meth)acrylate, neopentyl (meth)acrylate, hexyl (meth)acrylate, heptyl (meth)acrylate, n-octyl (meth)acrylate, and 2-ethyl hexyl (meth)acrylate.

Among the examples of the (b), the (b1) is preferred from the viewpoint of the demulsibility and the solubility, among which methyl methacrylate (hereinafter abbreviated as "MMA") is more preferred.

(c) Nitrogen Atom-containing Monomer:

Examples of the (c) include primary to tertiary amino group-containing vinyl monomers [dimethyl aminoethyl (meth)acrylate, diethyl aminoethyl (meth)acrylate, dimethyl aminoethyl (meth)acrylamide, morpholinoethyl (meth)acrylate, N-vinyl pyrrolidone, etc.], quaternary ammonium salt group-containing vinyl monomers [(meth)acryloyl oxyethyl trimethyl ammonium chloride, etc.], amphoteric vinyl monomers, and (meth)acrylonitrile. Among the examples of the (c), dimethyl aminoethyl (meth)acrylate, diethyl aminoethyl (meth)acrylate, and morpholinoethyl (meth)acrylate.

(d) Hydrocarbon Series Vinyl Monomer:

Examples of the (d) include alkene having 2 to 20 carbon atoms [ethylene, propylene, butene, isobutylene, diisobutylene, dodecene, etc.], alkadiene having 4 to 12 carbon atoms [butadiene, isoprene, 1,4-pentadiene, etc.], alicyclic hydrocarbon [cyclohexene, (di)cyclopentadiene, vinyl cyclohexene, ethylidene bicycloheptene, etc.], aromatic hydrocarbon series vinyl monomer [styrene, α-methyl styrene, vinyl toluene, etc.].

(e) Other Monomers:

Examples of the (e) include vinyl ester [vinyl acetate, vinyl propionate, etc.], vinyl ether [methyl vinyl ether, ethyl vinyl ether, etc.], vinyl ketone [methyl vinyl ketone, ethyl vinyl ketone, etc.], epoxy group-containing vinyl monomer [glycidyl (meth)acrylate, etc.], halogen-containing vinyl monomer [vinyl chloride, etc.], ester of unsaturated polycarboxylic acid [dimethyl maleate, dimethyl fumarate, dioctyl maleate, etc.], hydroxyl group-containing vinyl monomer [p-hydroxystyrene, 2-hydroxyethyl (meth)acrylate, (meth)allyl alcohol, etc.], polyoxyalkylene chain-containing vinyl monomer [polyethylene glycol mono(meth)acrylate, etc.], carboxyl group-containing vinyl monomer [(meth)acrylic acid, maleic acid, fumaric acid, maleic acid monoalkyl ester, etc.], and those produced by a method other than the method of the present invention among (meth)acrylic acid alkyl esters in which an alkyl group has 10 to 36 carbon atoms.

Among the (b) to (e) described above, the (b) is preferred from the viewpoint of the viscosity index improving ability, the low-temperature viscosity, the pour-point depressing ability, and the shearing stability, and the (c) is preferred from the viewpoint of the sludge dispersibility.

The lubricating oil additive of the present invention can be used as a viscosity index improver.

In the case where the polymer (P) is used as a viscosity index improver, the ratio by weight of the (a1), (a2), and (b1) in monomers that are constituents of the polymer (P) is as follows, from the viewpoint of the viscosity index and the solubility:

the (a1) preferably is 0.1 to 100%, more preferably 20 to 95%, particularly preferably 30 to 95%, further particularly preferably 40 to 95%, and most preferably 50 to 95%;

the (a2) preferably is 0 to 75%, more preferably 5 to 65%, particularly preferably 5 to 50%, further particularly preferably 5 to 40%, and most preferably 5 to 20%; and the (b1) preferably 0 to 45%, more preferably 5 to 40%, particularly preferably 10 to 35%, further particularly preferably 10 to 25%, and most preferably 10 to 22%.

In the case where the polymer (P) is used as a viscosity index improver, the ratio by weight of (b1)/(a) is 5/95 to 30/70, and more preferably 10/90 to 22/78.

Examples of the polymer (P) in the case where the (P) is used as a viscosity index improver include a copolymer of methyl methacrylate/methacrylic acid ester in which an alkyl group has 12 to 15 carbon atoms/methacrylic acid ester in which an alkylene group has 16 to 20 carbon atoms (0 to 22 wt %/20 to 90 wt %/0 to 20 wt %).

It should be noted that the percentage by weight of the (c) in monomers that are constituents of the polymer (P) in the case where the polymer (P) is used as a viscosity index improver normally is 0%, preferably 0.1 to 10% from the viewpoint of the sludge dispersibility, more preferably 1 to 7%, and particularly preferably 2 to 5%.

The lubricating oil additive of the present invention can be used as a pour-point depressant.

In the case where the polymer (P) is used as a pour-point depressant, the percentages by weight of the (a1), (a2), and (b1) in monomers that are constituents of the polymer (P) are as follows, from the viewpoints of the low-temperature viscosity and the solubility of the same in a diluent and a base oil:

the (a1) preferably 30 to 100%, more preferably 40 to 95%, and particularly preferably 50 to 90%;

the (a2) preferably is 0 to 70%, more preferably 5 to 60%, and particularly preferably 10 to 50%; and the (b1) preferably is 0 to 20%, more preferably 0 to 10%, and particularly preferably 0%.

The ratio by weight (b1)/(a) in the case where the polymer (P) is used as a pour-point depressant is 0/100 to 10/90, and more preferably 0/100.

In the case where the polymer (P) is used as a pour-point depressant, the average number of carbon atoms in an alkyl group of the (a) that is a constituent of the (P) is 12 to 16 preferably.

In the case where the (P) is used as a pour-point depressant, examples of the (P) include dodecyl methacrylate/hexadecyl methacrylate (10 to 50%/50 to 90%) copolymer [average number of carbon atoms: 14.0 to 15.6], dodecyl methacrylate/tetradecyl methacrylate (90 to 70%/10 to 30%) copolymer [average number of carbon atoms: 12.2 to 12.6]; and methacrylic acid ester of Dobanol 23/hexadecyl methacrylate/octadecyl methacrylate (30 to 70%/5 to 50%/3 to 20%) copolymer [average number of carbon atoms: 13.7 to 15.4].

It should be noted that in the case where the monomer (b) is used as a constituent monomer in the polymer (P) that is used as a viscosity index improver or a pour-point depressant, it is preferable that the average content of sulfur atoms, calculated from the content of sulfur atoms in the (b) and the content of sulfur atoms in the (a) preferably is not more than 50 ppm.

The weight-average molecular weight (hereinafter abbreviated as "Mw") of the polymer (P) preferably is 5,000 to 1,000,000, more preferably 15,000 to 500,000, and particularly preferably 20,000 to 400,000. The "Mw" of the present invention is measured by gel permeation chromatography (GPC), relative to polystyrene as a certified reference material.

Regarding the adjustment of the Mw, the Mw can be adjusted by, for example, controlling the temperature upon polymerization, the monomer concentration (diluent concentration), the amount of catalyst, the amount of chain transfer agent, etc.

The polymer (P) can be obtained by a known producing method. For example, the polymer (P) can be obtained by subjecting the monomer described above to radical polymerization in the presence of a polymerization catalyst, by using the diluent (D) as required.

A diluent having a flash point of preferably 120° C. or above, more preferably 130° C. or above, and particularly preferably 160° C. or above is preferred as the diluent (D).

Examples of the diluent having a flash point of 120° C. or above include "YUBASE 2" (produced by SK Corporation, flash point: 160° C.) and "YUBASE 3" (produced by SK Corporation, flash point: 194° C.).

In the lubricating oil additive of the present invention, the diluent (D) used in the process for the production of the polymer (P) may be removed after the production, or may remain therein.

In the case where the diluent (D) remains therein, the lubricating oil additive of the present invention contains normally not more than 80 wt %, preferably not more than 60 wt % of the diluent (D).

The lubricating oil composition of the present invention contains the above-described lubricating oil additive and a base oil.

Examples of the base oil include mineral oils and synthetic lubricating oils.

Among these, high-viscosity-index oils that contain isoparaffine and/or that is obtained by hydrogenolysis, poly-α-olefin-type synthetic lubricating oils, and ester-type synthetic lubricating oils are preferred. They may be used alone or in combination of two or more.

The base oil preferably has a kinematic viscosity of 2 to 10 mm$^2$/s at 100° C. and a flash point of 160° C. or above.

Further, the base oil preferably has a viscosity index of not less than 80, more preferably not less than 100, and particularly preferably 105 to 180. By using such a base oil, the index viscosity is improved further, whereby the fuel economy is improved further.

Still further, the base oil has a cloudy point (JIS K2269-1993) of −5° C. or below, preferably −15° C. to −60° C. With the cloudy point of the base oil in the foregoing range, the deposited amount of wax is small, whereby a preferable low-temperature viscosity is achieved.

The lubricating oil composition of the present invention contains 0.1 to 30 wt % of the polymer (P) based on the weight of the lubricating oil composition.

The lubricating oil composition of the present invention may contain an additive (C) known conventionally. Examples of the additive (C) include a dispersant, a cleaning agent, an antioxidant, an antifoaming agent, an oiliness improver, a friction/abrasion regulating agent, an organophosphorus compound, an extreme-pressure agent, a demulsifier, and a corrosion inhibitor. The added amount of each additive (C) usually is not more than 10 wt %, and preferably not more than 5 wt %, based on the weight of the lubricating oil composition.

The kinematic viscosity of the lubricating oil composition of the present invention at 100° C. preferably is 2 to 16 mm$^2$/s.

The lubricating oil composition of the present invention suitably is used as gear oils such as differential gear oils and industrial gear oils, transmission oils such as manual transmission oils, automatic transmission oils, and belt-CVTF, traction oils such as toroidal-CVT oils, hydraulic oils such as shock absorber oils, power-assisted steering oils, construction equipment hydraulic oils, and industrial hydraulic oils, as well as engine oils. The lubricating oil composition of the present invention more suitably is used as construction equipment hydraulic oils and industrial hydraulic oils among those described above.

EXAMPLE

The following describes the present invention in detail by referring to examples, though the present invention is not limited to these. It should be noted that "part" herein refers to "part by weight".

<Production Example of Sulfonic Acid Group-carrying Inorganic Porous Material (α)>

Production Example 1

200 parts of silica gel ("Wakogel C-100" produced by Wako Pure Chemical Industries, Ltd.) that had been washed with ion exchange water and thereafter dried preliminarily, 400 parts of toluene and 10 parts of water as solvent were put in a reaction container equipped with an agitator, a heating/cooling device, a thermometer, and a reflux pipe, and the temperature thereof was raised to 100 to 110° C. Then, 100 parts of 3-mercaptopropyl trimethoxysilane was added thereto, and the mixture was agitated under reflux for 8 hours so as to react. Thereafter, 15 parts of water was added thereto, and the mixture was allowed to react for 8 hours further. Solid components were separated from the reaction mixture by filtering, and were washed with 400 parts of toluene three times, and then with 400 parts of isopropyl alcohol three times. Thereafter, the components were dried under a reduced pressure at 120° C. for 5 hours. As a result, 190 parts of a silane coupling agent-carrying inorganic porous material was obtained.

150 parts of the silane coupling agent-carrying inorganic porous material, 450 parts of methanol as solvent, and 150 parts of 30% hydrogen peroxide water were put in the same reaction container as that described above, and were allowed to react under reflux at 70° C. for 8 hours. Solid components were separated from the reaction mixture by filtering, and were washed with 400 parts of methanol three times, with 400 parts of 0.1 N sulfuric acid once, and with 400 parts of ion exchange water three times in the stated order. Thereafter, the solid components were dried under a reduced pressure at 120° C. for 5 hours. As a result, 140 parts of a catalyst (α-1) made of a sulfonic acid group-carrying inorganic porous material was obtained. The (α-1) had a structure such that silica gel carried a sulfopropyl group, and had a d50 of 230 μm, a BET specific surface area of 222 m$^2$/g, an acid value of 37 mgKOH/g, and an aspect ratio of 1.89.

Production Example 2

190 parts of a silane coupling agent-carrying inorganic porous material was obtained by the same method as that for the production example 1 except that 200 parts of phenyl triethoxysilane was used in place of 3-mercapto propyl trimethoxysilane.

150 parts of the silane coupling agent-carrying inorganic porous material, and 180 parts of dichloroethane as solvent were put in a reaction container, and 10 parts of sulfur trioxide was dropped thereto at 17 to 23° C. over 5 hours. Thereafter, the mixture was agitated at 40 to 50° C. for 3 hours so as to be sulfonated. After 4 parts of ion exchange water was added thereto so that non-reacted sulfur trioxide was transformed to sulfuric acid, solid components were separated from the reaction mixture by filtering. The solid components were washed with 400 parts of isopropyl alcohol three times, and then with 400 parts of ion exchange water three times. Thereafter, the solid components were dried under a reduced pressure at 120° C. for 5 hours. As a result, 140 parts of a catalyst (α-2) was obtained. The (α-2) had a structure such that silica gel carried a sulfophenyl group, and had a d50 of 230 μm, a BET specific surface area of 215 m$^2$/g, an acid value of 45 mgKOH/g, and an aspect ratio of 1.82.

Production Example 3

140 parts of a catalyst (α-3) was obtained by the same method as that for Production Example 1 except that 200 parts of a silica-alumina-based porous material ("KYOWAAD 700 SN" produced by Kyowa Chemical Industry Co., Ltd) was used as a catalyst carrier. The (α-3) had a structure such that a silica-alumina-based porous material carried a sulfopropyl group, and had a d50 of 216 μm, a BET specific surface area of 197 m$^2$/g, an acid value of 85 mgKOH/g, and an aspect ratio of 1.12.

Production Example 4

140 parts of a catalyst (α-4) was obtained by the same method as that for Production Example 1 except that 200 parts of alumina ("Alumina Activated 200" produced by Nacalai Tesque) was used as a catalyst carrier. The (α-4) had a structure such that alumina carried a sulfopropyl group, and had a d50 of 68 μm, a BET specific surface area of 231 m$^2$/g, an acid value of 52 mgKOH/g, and an aspect ratio of 1.14.

Production Example 5

140 parts of a catalyst (α-5) was obtained by the same method as that for Production Example 1 except that 200 parts of silica gel ("CARiACT Q-6", particle diameter range of contained particles: 75 to 500 μm, produced by Fuji Silysia Chemical Ltd.) was used as a catalyst carrier. The (α-5) had a structure such that silica gel carried a sulfopropyl group, and had a d50 of 220 μm, a BET specific surface area of 287 m$^2$/g, an acid value of 43 mgKOH/g, and an aspect ratio of 1.02.

Production Example 6

140 parts of a catalyst (α-6) was obtained by the same method as that for Production Example 1 except that 200 parts of silica gel ("CARiACT Q-6", particle diameter range of contained particles: 45 to 75 μm, produced by Fuji Silysia Chemical Ltd.) was used as a catalyst carrier. The (α-6) had a structure such that silica gel carried a sulfopropyl group, and had a d50 of 58 μm, a BET specific surface area of 320 m$^2$/g, an acid value of 34 mgKOH/g, and an aspect ratio of 1.02.

<Production of α,β-Unsaturated Carboxylic Acid Ester>

Example 1

1,800 parts of lauryl alcohol and 1,100 of methacrylic acid (molar ratio=1:1.3) were put in a reaction container equipped with an agitator, a heating/cooling device, a thermometer, and a water separation pipe, and 580 parts of the catalyst (α-1) and 0.3 part of hydroquinone as a polymerization inhibitor were added thereto. An esterification reaction was allowed to occur at a reaction temperature of 115 to 125° C. for 2 hours while generated water was removed to the outside continuously via the water separation pipe. Then, the reaction was continued further for one hour under a reduced pressure of 250 to 300 mmHg at 115 to 125° C. After excess portions of methacrylic acid were removed by distillation at 10 to 20 mmHg and 120 to 130° C., the reaction product was cooled, and the catalyst was removed by decantation. As a result, 2,500 parts of an unsaturated carboxylic acid ester (E-1) of the present invention was obtained.

As a result of H$^1$-NMR analysis, the (E-1) contained 99.8 mol % of lauryl methacrylate ester as a desired product, and 0.2 mol % of non-reacted alcohol. Elimination reaction products, by-product etherification products, and by-product addition products were below the detection limits (not more than 0.1 mol % each).

To determine an amount of components derived from sulfonic acid groups eluted from the catalyst to the obtained product, the S content was quantified by the ICP device "ICPS-8000" (manufactured by Shimadzu Corporation). Consequently, the amount was below the detection limit (not more than 20 ppm).

Examples 2 to 8

α,β-unsaturated carboxylic acid esters (E-2) to (E8) of Examples 2 to 8 were produced in the same manner as that for Example 1 except that raw materials shown in Table 1 below were used, the numbers of parts thereof being shown in Table 1 also, respectively.

Results of Analysis of Products Obtained are Shown in Table 2.

Example 9

5.7 kg of a mixture of alkyl alcohols having 12 carbon atoms and having 13 carbon atoms ("Dobanol 23" produced by Mitsubishi Chemical Corporation), 3.3 kg of methacrylic acid (molar ratio=1:1.3), and 1 kg of hydroquinone as a polymerization inhibitor were put in a 12-liter vessel made of stainless steel, equipped with an agitator, a heating/cooling device, a thermometer, a gas inlet, a condenser, and a pit. A mixture gas of air and nitrogen (1:2) was passed at a rate of 500 ml/min throughout the entire process. After the temperature was raised to the reaction temperature of 115 to 125° C., the reaction liquid in the vessel was passed by a diaphragm pump through a fixed bed made of stainless steel, filled with 1.8 kg of the catalyst (α-5), at a flow rate of 1.1 liter/min continuously. The liquid discharged therefrom was circulated to the vessel, while generated water was removed by distillation under a normal pressure at 115 to 125° C. in the vessel. Thus, the reaction and dehydration were carried out concurrently and continuously for one hour while the reaction liquid was circulated.

Thereafter, the pressure in the vessel was reduced to 250 to 300 mmHg, and the same reaction and dehydration were carried out further for two hours, so that the esterification reaction was completed. Subsequently, all of the reaction liquid was returned to the vessel, and an excess portion of methacrylic acid was removed by distillation under conditions of 10 to 20 mmHg and 120 to 130° C. As a result, 7.6 kg of an α,β-unsaturated carboxylic acid ester composition (E-9) of the present invention was obtained.

It should be noted that an average residence time of the reaction liquid in the fixed bed per one passage was 2.5 minutes.

Further, from the flow rate in the fixed bed, it was calculated that the entire amount of the reaction liquid in the esterification reaction was circulated about 18 times.

Results of analysis of the obtained product are shown in Table 2.

Example 10

An α,β-unsaturated carboxylic acid ester composition (E-10) of Example 10 was produced in the same manner as that for Example 9 except that the flow rate for passing the liquid was 3.1 liter/min, and the average residence time in the fixed bed per one passage was 0.8 minute.

From the flow rate and the average residence time in the fixed bed, it was calculated that the entire amount of the reaction liquid was circulated about 50 times under a normal pressure.

Results of analysis of the obtained product are shown in Table 2.

Comparative Examples 1 to 4

α,β-unsaturated carboxylic acid esters (H-1) to (H-4) of Comparative Examples 1 to 4 were obtained by esterification in the same manner as that for Examples 1 to 4 except that sulfuric acid was used as a catalyst, the number of parts of the sulfuric acid used being shown in Table 3, then neutralization with use of aqueous solution of sodium hydroxide and separation, and thereafter washing with ion exchange water and separation.

Results of analysis of the obtained products are shown in Table 4.

Comparative Example 5

An α,β-unsaturated carboxylic acid ester (H-5) of Comparative Example 5 was produced in the same manner as that for Example 1 except that a polystyrene sulfonic acid-type ion exchange resin "AMBERLYST 16" (produced by Rohm & Haas Company) was used as a catalyst, the number of parts of the same used being shown in Table 3. "AMBERLYST 16" had a d50 of 720 μm, a BET specific surface area of 35 m²/g, an acid value of 280 mgKOH/g, and an aspect ratio of 1.05.

Results of analysis of the obtained product are shown in Table 4.

Comparative Example 6

An α,β-unsaturated carboxylic acid ester (H-6) of Comparative Example 6 was produced in the same manner as that for Comparative Example 5 except that acrylic acid was used as the (B), the number of parts of 5 the acrylic acid used being shown in Table 3.

Results of analysis of the obtained product are shown in Table 4.

TABLE 1

| | Product | Example 1 E-1 | Example 2 E-2 | Example 3 E-3 | Example 4 E-4 | Example 5 E-5 | Example 6 E-6 | Example 7 E-7 | Example 8 E-8 |
|---|---|---|---|---|---|---|---|---|---|
| A | Lauryl alcohol | 1,800 | — | — | — | — | — | — | 1,800 |
| | Myristyl alcohol | — | 1,800 | — | — | — | — | — | — |
| | Cetyl alcohol | — | — | 1,800 | — | 1,800 | — | — | — |
| | Stearyl alcohol | — | — | — | 1,800 | — | — | — | — |
| | EO 4 mole adduct of stearyl alcohol | — | — | — | — | — | 1,800 | — | — |
| | Neopentyl glycol | — | — | — | — | — | — | 1,800 | — |
| B | Methacrylic acid | 1,100 | 940 | 830 | 750 | — | 450 | — | 1,100 |
| | Acrylic acid | — | — | — | — | 700 | — | 2,870 | — |
| | Hydroquinone | 0.3 | 0.3 | 0.2 | 0.2 | 0.2 | 0.1 | 1.4 | 0.3 |
| α | α-1 | 580 | 550 | 530 | 510 | — | — | — | — |
| | α-2 | — | — | — | — | — | 450 | — | — |

TABLE 1-continued

|  | Example | | | | | | | |
|---|---|---|---|---|---|---|---|---|
| Product | 1 E-1 | 2 E-2 | 3 E-3 | 4 E-4 | 5 E-5 | 6 E-6 | 7 E-7 | 8 E-8 |
| α-3 | — | — | — | — | 500 | — | — | — |
| α-4 | — | — | — | — | — | — | 930 | — |
| α-5 | — | — | — | — | — | — | — | 580 |
| AMBERLYST 16 | — | — | — | — | — | — | — | — |
| Sulfuric acid | — | — | — | — | — | — | — | — |

TABLE 2

|  | Example | | | | | | | | | |
|---|---|---|---|---|---|---|---|---|---|---|
| Product | 1 E-1 | 2 E-2 | 3 E-3 | 4 E-4 | 5 E-5 | 6 E-6 | 7 E-7 | 8 E-8 | 9 E-9 | 10 E-10 |
| Principal component (mol %) | 99.8 | 99.8 | 99.8 | 98.8 | 99.6 | 99.9 | 99.9 | 99.8 | 99.2 | 99.7 |
| Non-reacted alcohol (mol %) | 0.2 | 0.2 | 0.2 | 0.2 | 0.3 | 0.1 | 0.1 | 0.2 | 0.8 | 0.3 |
| Elimination reaction products (mol %) | N.D. | N.D. | N.D. | N.D. | N.D. | N.D. | N.D. | N.D. | N.D. | N.D. |
| By-product etherification products (mol %) | N.D. | N.D. | N.D. | N.D. | N.D. | N.D. | N.D. | N.D. | N.D. | N.D. |
| By-product addition products (mol %) | N.D. | N.D. | N.D. | N.D. | 0.1 | N.D. | 0.2 | N.D. | N.D. | N.D. |
| S content (ppm) | N.D. | N.D. | N.D. | N.D. | N.D. | N.D. | N.D. | N.D. | N.D. | N.D. |

N.D.: Not detected (i.e. below the detection limit)

TABLE 3

|  |  | Comparative Example | | | | | |
|---|---|---|---|---|---|---|---|
|  | Product | 1 H-1 | 2 H-2 | 3 H-3 | 4 H-4 | 5 H-5 | 6 H-6 |
| A | Lauryl alcohol | 1,800 | — | — | — | 1,800 | 1,800 |
|  | Myristyl alcohol | — | 1,800 | — | — | — | — |
|  | Cetyl alcohol | — | — | 1,800 | — | — | — |
|  | Stearyl alcohol | — | — | — | 1,800 | — | — |
|  | EO 4 mole adduct of stearyl alcohol | — | — | — | — | — | — |
|  | Neopentyl glycol | — | — | — | — | — | — |
| B | Methacrylic acid | 1,100 | 940 | 830 | 750 | 1,100 | — |
|  | Acrylic acid | — | — | — | — | — | 910 |
|  | Hydroquinone | 0.3 | 0.3 | 0.2 | 0.2 | 0.3 | 0.3 |
| α | α-1 | — | — | — | — | — | — |
|  | α-2 | — | — | — | — | — | — |
|  | α-3 | — | — | — | — | — | — |
|  | α-4 | — | — | — | — | — | — |
|  | α-5 | — | — | — | — | — | — |
|  | AMBERLYST 16 | — | — | — | — | 580 | 580 |
|  | Sulfuric acid | 7.2 | 7.2 | 7.2 | 7.2 | — | — |

TABLE 4

|  | Comparative Example | | | | | |
|---|---|---|---|---|---|---|
| Product | 1 H-1 | 2 H-2 | 3 H-3 | 4 H-4 | 5 H-5 | 6 H-6 |
| Principal component (mol %) | 98.9 | 98.8 | 98.8 | 98.6 | 89.1 | 88.1 |
| Non-reacted alcohol (mol %) | 1.0 | 1.1 | 1.1 | 1.2 | 0.3 | 0.4 |
| Elimination reaction products (mol %) | N.D. | N.D. | N.D. | N.D. | 4.0 | 4.1 |
| By-product etherification products (mol %) | N.D. | N.D. | N.D. | N.D. | 6.4 | 5.8 |
| By-product addition products (mol %) | 0.1 | 0.1 | 0.1 | 0.2 | 0.2 | 1.6 |
| S content (ppm) | 100 | 99 | 133 | 128 | 70 | 70 |

N.D.: Not detected (i.e. below the detection limit)

As seen in Tables 2 and 4, the α,β-unsaturated carboxylic acid esters of the present invention exhibit a high purity with only a smaller amount of by-products, and contain only a smaller amount of catalyst residues.

Example 11

25 parts of a diluent "YUBASE 2" (produced by SK Corporation) was put in a reaction container equipped with an agitator, a heating/cooling device, a thermometer, a dropping funnel, and a nitrogen blowing pipe. On the other hand, 100 parts in total of methyl methacrylate (produced by Mitsubishi Gas Chemical Co., Ltd., the sulfur content: not more than 10 ppm) and monomers shown Table 5, and 2,2'-azobis(2,4-dimethyl valeronitrile) (hereinafter abbreviated as ADVN), amount of which was according to Table 5, were put as a radical polymerization initiator in another glass beaker, stirred at 20° C. so as to be mixed, whereby a monomer solution was prepared. The monomer solution was put in the dropping funnel. Nitrogen was introduced into the reaction container so that the gas phase part therein was substituted with nitrogen, whereby the gas-phase oxygen concentration was set to 500 to 1,000 ppm. In a sealed state, the monomer solution was dropped at 85° C. over four hours. For two hours after the completion of dropping, aging was carried out at 85° C., and low-boiling-point components were removed from the obtained polymer by distillation at 130° C. for three hours and under a reduced pressure of 4 kPa or less over two hours. Then, the obtained polymer was diluted with "YUBASE 2" so as to have a concentration of 60 wt %. Thus, a lubricating oil additive (A-1) was obtained. The Mw measurement result of the same is shown in Table 5. The polymer contained in the (A-1) is suitable as a viscosity index improver.

Examples 12, 13, and Comparative Examples 7 to 9

Lubricating oil additives (A-2) and (A-3) of the present invention, and diluted liquids of comparative lubricating oil additives (X-1), (X-2), and (X-3) were obtained in the same manner as that for Example 11 except that the types of the monomers used therein and the numbers of parts thereof were as shown in Table 5.

The polymer contained in the (A-2) is suitable as a viscosity index improver, and the polymer contained the (A-3) is suitable as a pour-point depressant. The (X-1) and the (X-2) were used for comparison with the (A-1) and the (A-2), respectively, and the (X-3) was used for comparison with the (A-3).

The Mw measurement results are shown in Table 5.

The measurement of Mw by GPC was performed under the following conditions:
Apparatus: HLC-802A produced by TOSOH Corporation
Column: TSK gel GMH6, two columns
Measurement temperature: 40° C.
Sample solution: 0.5 wt % THF solution
Injected amount of solution: 200 µl
Detection apparatus: refractometer
Reference material: polystyrene

TABLE 5

|  | Ex. 11 A-1 | Ex. 12 A-2 | Ex. 13 A-3 | Comp. Ex. 7 X-1 | Comp. Ex. 8 X-2 | Comp. Ex. 9 X-3 |
|---|---|---|---|---|---|---|
| Monomer |  |  |  |  |  |  |
| MMA | 15 | 20 | — | 15 | 20 | — |
| E-1 | 70 | 45 | 50 | — | — | — |
| E-2 | 8 | 25 | 10 | — | — | — |
| E-3 | 5 | 7 | 28 | — | — | — |
| E-4 | 2 | 3 | 12 | — | — | — |
| H-1 | — | — | — | 70 | 45 | 50 |
| H-2 | — | — | — | 8 | 25 | 10 |
| H-3 | — | — | — | 5 | 7 | 28 |
| H-4 | — | — | — | 2 | 3 | 12 |
| ADVN | 0.4 | 0.4 | 0.4 | 0.4 | 0.4 | 0.4 |
| Mw | 120,000 | 120,000 | 120,000 | 120,000 | 120,000 | 120,000 |

<Preparation of Lubricating Oil Composition and Evaluation Test>

Examples 14 to 17 and Comparative Examples 10 to 13

The (A-1) to (A-3) and the (X-1) to (X-3) were mixed with a base oil 1 (kinematic viscosity at 100° C.: 4.3 mm$^2$/s, kinematic viscosity at 40° C.: 20.3 MM$^2$/s, viscosity index: 121) so as to be dissolved in the base oil 1, parts by weight thereof being shown in Table 6, whereby lubricating oil compositions were prepared.

The low-temperature viscosities, the viscosity indices, the pour points, the shear stabilities, and the demulsibilities thereof were evaluated by the following methods.

The results are shown in Table 6.

<Low-temperature Viscosity Test Method>
A viscosity at −40° C. was measured by the method according to JPI-5S-26-85.

<Viscosity Index Test Method>
A viscosity index was determined by the method according to JIS K2283.

<Shear Stability Test Method>
A kinematic viscosity decreasing ratio at 100° C. was calculated by the method according to JASO M347-95.

<Kinematic Viscosity Measurement Method>
A kinematic viscosity was measured by the method according to JIS K2283.

<Demulsibility Test Method>
A demulsibility after 30 minutes was evaluated according to JIS K2520. A better demulsibility was obtained as a volume of an emulsion layer was smaller.

<Pour Point Measurement Method>
A pour point was measured by the method according to JIS K2269.

TABLE 6

|  |  | Used viscosity index improver or pour point depressant |  | Amount of base oil 1 | Evaluation Result |  |  |  |  |  |
|---|---|---|---|---|---|---|---|---|---|---|
|  |  | Product | Amount |  | Low-temperature viscosity at −40° C. | Viscosity index | Shear stability (%) | Kinematic viscosity at 40° C. (mm$^2$/s) | Pour point (° C.) | Demulsibility Oil-water-emulsion layer (ml) |
| Example | 14 | A-1 | 8 | 92 | 8500 | 7.22 | 19 | 30.78 | — | 37-38-5 |
|  | 15 | A-2 | 8 | 92 | 9000 | 7.22 | 19 | 30.79 | — | 37-38-5 |
|  | 16 | A-3 | 0.5 | 99.5 | — | — | — | — | −42.5 | 37-38-5 |
|  | 17 | A-1 | 8 | 91.7 | 7800 | 7.23 | 19 | 30.88 | — | 37-38-5 |
|  |  | A-3 | 0.3 |  |  |  |  |  |  |  |
| Comparative | 10 | X-1 | 8 | 92 | 8600 | 7.22 | 19 | 30.79 | — | 25-35-20 |
| Example | 11 | X-2 | 8 | 92 | 9000 | 7.22 | 19 | 30.76 | — | 25-35-20 |
|  | 12 | X-3 | 0.5 | 99.5 | — | — | — | — | −42.5 | 25-35-20 |

TABLE 6-continued

| | Used viscosity index improver or pour point depressant | | Amount of base oil 1 | Evaluation Result | | | | | |
|---|---|---|---|---|---|---|---|---|---|
| | | | | Low-temperature viscosity at −40° C. | Viscosity index | Shear stability (%) | Kinematic viscosity at 40° C. (mm²/s) | Pour point (° C.) | Demulsibility Oil-water-emulsion layer (ml) |
| | Product | Amount | | | | | | | |
| 13 | X-1 X-3 | 8 0.3 | 91.7 | 7850 | 7.23 | 19 | 30.90 | — | 25-35-20 |

As clear from Table 6, the lubricating oil additives of the present invention were excellent regarding not only the low-temperature viscosity, the viscosity index, the pour point, and the shear stability, but also the demulsibility.

INDUSTRIAL APPLICABILITY

The present invention can provide a method for producing an α,β-unsaturated carboxylic acid ester that does not involve generation of a large amount of waste products, a method for producing a high-purity α,β-unsaturated carboxylic acid ester that causes only a smaller amount of by-products to be generated, and a method for producing an α,β-unsaturated carboxylic acid ester that contains only a smaller amount of catalyst residues and exhibits less metal corrosion behavior. Further, the present invention can provide high-purity α,β-unsaturated carboxylic acid esters obtained by the above-described producing methods. Therefore, the present invention can be used effectively in production of α,β-unsaturated carboxylic acid esters.

The invention claimed is:

1. A method for producing an α,β-unsaturated carboxylic acid ester, the method comprising:
   (1) causing an alcohol (A) to react with an α,β-unsaturated carboxylic acid or a lower alkyl ester (B) of the α,β-unsaturated carboxylic acid (B) by flow processing in the presence of a sulfonic acid group-carrying inorganic porous material (α), and
   (2) removing water or lower alcohol generated as a result of the reaction between the (A) and the (B) from the reaction mixture obtained,
   wherein
   the steps (1) and (2) are repeated 3 to 200 times,
   a functional group on a surface of the inorganic porous material is covalently bonded with a sulfonic acid group-containing entity, and
   the sulfonic acid group-carrying inorganic porous material (α) is obtained by causing an inorganic porous material to react with at least one of sulfonic acid precursor group-containing compounds so that a sulfonic acid precursor group-carrying inorganic porous material is obtained, and thereafter transforming the sulfonic acid precursor group to a sulfonic acid group.

2. The method for producing an α,β-unsaturated carboxylic acid ester according to claim 1, wherein the (A) is a monohydric alcohol, a polyhydric alcohol having a valence of two to eight, or an alkylene oxide adduct of the monohydric alcohol or the polyhydric alcohol.

3. The method for producing an α,β-unsaturated carboxylic acid ester according to claim 1, wherein the (B) is an acrylic acid or a methacrylic acid.

4. The method for producing an α,β-unsaturated carboxylic acid ester according to claim 1, wherein the (α) is a granular inorganic porous material made of one or more inorganic materials selected from the group consisting of silica, alumina, titania, magnesia, and zirconia, the inorganic porous material carrying a sulfonic acid group.

5. The method for producing an α,β-unsaturated carboxylic acid ester according to claim 1, wherein the (α) is a granular material having an average particle diameter of 1 to 8,000 μm.

6. The method for producing an α,β-unsaturated carboxylic acid ester according to claim 1, wherein the (α) has a BET specific surface area of not less than 30 m²/g.

7. The method for producing an α,β-unsaturated carboxylic acid ester according to claim 1, wherein the (α) has an acid value of 5 to 250 mgKOH/g.

8. The method for producing an α,β-unsaturated carboxylic acid ester according to claim 1, wherein the (α) is in a spherical particle form having an aspect ratio of 1.0 to 1.25.

9. The method for producing an α,β-unsaturated carboxylic acid ester according to claim 1, wherein in the step (2), air or a mixture gas composed of air and nitrogen is passed through the reaction mixture.

10. The method for producing an α,β-unsaturated carboxylic acid ester according to claim 1, wherein, a flow processing container for the step (1) and a vessel for the step (2) are connected so that a reaction liquid for the steps (1) and (2) is circulating through the container and the vessel and the steps (1) and (2) are repeated concurrently and continuously.

* * * * *